United States Patent [19]  [11] 4,146,627
Wehinger et al.  [45] Mar. 27, 1979

[54] AMINOALKYLIDEAMINO-1,4-DIHY-
DROPYRIDINES AND THEIR USE AS
MEDICAMENTS

[75] Inventors: Egbert Wehinger, Velbert; Friedrich Bossert, Wuppertal; Horst Meyer, Wuppertal; Wulf Vater, Wuppertal; Arend Heise, Wuppertal; Stanislav Kaada, Wuppertal; Kurt Stoepel, Wuppertal, all of Fed. Rep. of Germany

[73] Assignee: Bayer Aktiengesellschaft, Leverkusen, Fed. Rep. of Germany

[21] Appl. No.: 828,136

[22] Filed: Aug. 26, 1977

[30] Foreign Application Priority Data
Sep. 1, 1976 [DE] Fed. Rep. of Germany ....... 2639257

[51] Int. Cl.$^2$ ................. C07D 213/55; A61K 31/455
[52] U.S. Cl. ........................... 424/266; 260/244.4; 542/424; 544/238; 544/333; 544/284; 544/353; 544/405; 546/257; 546/258; 546/281; 546/294; 546/306; 546/296; 546/297; 546/261; 546/262; 546/263; 546/256; 546/271; 546/279; 546/278; 546/273; 546/280; 546/275; 546/144; 546/167
[58] Field of Search ................ 260/295.5 R, 294.9, 260/294.8 G, 294.8 F, ; 424/266; 542/424

[56] References Cited
U.S. PATENT DOCUMENTS 3,946,026  3/1976  Meyer et al. ............ 260/295.5 R
3,959,292  5/1976  Meyer et al. ............ 260/295.5 R

*Primary Examiner*—Alan C. Rotman
*Attorney, Agent, or Firm*—Sprung, Felfe, Horn, Lynch & Kramer

[57] ABSTRACT

The circulation provides new aminoalkylidene-amino-1,4-dihydropyridines which influence the circulatory system and are useful, for instance, as antihypertensive agents. Also included in the invention are methods for the preparation of said dihydropyridines, compositions containing them and methods for their use.

12 Claims, No Drawings

AMINOALKYLIDEAMINO-1,4-DIHYDROPYRIDINES AND THEIR USE AS MEDICAMENTS

The present invention relates to new aminoalkylideneamino-1,4-dihydropyridines, several processes for their preparation and their use as medicaments, in particular as agents which influence the circulatory system.

It has already been disclosed that 2,6-dimethyl-4-phenyl-1,4-dihydropyridine-3,5-dicarboxylic acid diethyl ester is obtained when benzylideneacetoacetic acid ethyl ester is reacted with β-amino-crotonic acid ethyl ester or acetoacetic acid ethyl ester and ammonia (Knoevenagel, Ber. dtsch.chem. Ges. 31, 743 1898)).

Furthermore, it is known that certain 1,4-dihydropyridines have interesting pharmacological properties (F. Bossert and W. Vater, Naturwissenschaften 58, 578 (1971)).

The present invention provides aminoalkylideneamino-1,4-dihydropyridines of the formula I

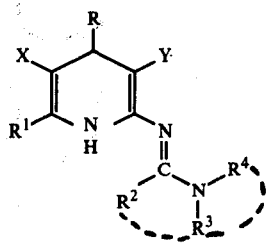

in which

R represents an aryl radical or a thienyl, furyl, pyrryl, pyrazolyl, imidazolyl, oxazolyl, isoxazolyl, thiazolyl, pyridyl, pyridiazinyl, pyrimidyl, pyrazinyl, quniolyl, isoquinolyl, indolyl, benzimidazolyl, quinazolyl or quinoxalyl radical, the aryl radical or the said heterocyclic radical optionally containing from 1 to 3 identical or different substituents selected from phenyl, alkyl, alkylene, alkenyl, alkinyl, alkoxy, alkenoxy, alkinoxy, dioxyalkylene, halogen, trifluoromethyl, trifluoromethoxy, dialkylamino, nitro, cyano, axido, carbalkoxy and $SO_m$-alkyl (where m = 0, 1 or 2), X and Y are identical or different and each represents the group $-S(O)_n-R^5$ or $-CO-R^6$, where n, $R^5$ and $R^6$ are as defined below.

$R^1$ represents hydrogen, a straight-chain or branched alkyl radical, an aryl radical or an aralkyl radical, $R^2$ represents hydrogen or a straight-chain or branched alkyl radical, it being possible for the alkyl radical optionally to form, together with the structural moiety

a five membered to seven membered heterocyclic ring in the manner indicated by the broken lines, or represents an aralkyl radical and $R^3$ and $R^4$ are identical or different and each represents a straight chain or branched alkyl radical, an alkoxyalkyl radical or an aralkyl radical or $R^3$ and $R^4$ conjointly with the nitrogen atom to which they are attached, form a 5 to 7-membered ring which is optionally substituted and which can contain an oxygen, sulphur or nitorgen atom as a further hetero-atom.

In the radicals $-S(O)_n-R^5$ and $-CO-R^6$, n represents 0, 1 or 2, $R^5$ represents a straight-chain, branched or cyclic, saturated or unsaturated aliphatic hydrocarbon radical which is optionally interrupted by 1 to 2 oxygen atoms in the chain or ring or in which a hydrogen atoms is replaced by a phenoxy or phenyl group, which is itself optionally substituted by halogen, cyano, dialkylamino, alkoxy, alkyl, trifluoromethyl or nitro, or is replaced by an α, β- or γ-pyridyl group or by an amino group, this amino group carrying two identical or different substituents selected from alkyl, alkoxyalkyl, aryl and aralkyl and these substituents optionally forming, with the nitorgen atom, a 5 to 7-memebered ring which can contain, as a further hetero-atom, an oxygen or sulphur atom or the N-alkyl grouping, or represnts an aryl radical which optionally contains 1 to 3 identical or different substituents selected from alkyl, alkoxy, halogen, cyano, trifuoromethyl, trifluoromethoxy, dialkylamino and nitro and $R^6$ represents alkyl, aryl, aralkyl or a dialkylamino group or represents the group $-OR^7$, wherein $R^7$ represents a straight-chain, branched or cyclic, saturated or unsaturated hydrocarbon radical which is optionally interrupted by 1 or 2 oxygen atoms in the chain or ring or in which a hydrogen atom is replaced by a phenoxy or phenyl group, which is itself optionally substituted by halogen, cyano, dialkylamino, alkoxy, alkyl, trifluoromethyl or nitro, or replaced by an α-, β- or γ-pyridyl group or by an amino group, this amino group carrying two identical or different substituents from the group alkyl, alkoxyalkyl, aryl and aralkyl and these substituents optionally forming, with the nitrogen atom, a 5- to 7-membered ring which can contain, as a further hetero-atom, an oxygen or sulphur atom or an N-alkyl group.

Furthermore, it has been found that the compounds of the invention are obtained when 2-amino-1,4-dihydropyridines of the formula II

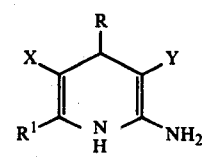

in which

R, $R^1$, X and Y have the meaning indicated above, are reacted, according to the known methods for converting an amino group into an aminoalkylideneamino group, with acid amide derivatives, such as, for example, (a) acid amide-phosphorus oxychloride adducts of the formula III

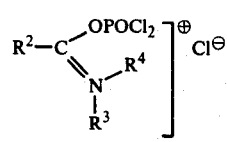

in which $R^2$, $R^3$, and $R^4$ have the meaning indicated above, or (b) orthocarboxylic acid amide diesters of the formula IV

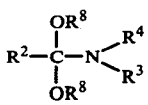

in which

R$^2$, R$^3$ and R$^4$ have the meaning indicated above and R$^8$ represents a lower alkyl group, or (c) orthocarboxylic acid diamide esters of the formula V

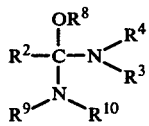

R$^2$, R$^3$ and R$^4$ have the meaning indicated above and R$^8$, R$^9$ and R$^{10}$ represent a lower alkyl group or (d) alkoxy-dialkylamino-nitriles of the formula VI

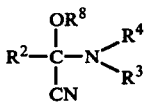

in which

R$^2$, R$^3$, and R$^4$ have the meaning indicated above and R$^8$ represents a lower alkyl group, optionally in the presence of inert solvents.

A resulting basic compound can be converted into a corresponding acid addition salt, for example by reacting it with an inorganic or organic acid, such as therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic propionic, succinic, glycollic, lactic, malic, tartaric, citric, ascorbic, maleic, hydroxymaleic, pyroracemic, phenlacetic, benoic, 4-aminobenzoic, anthranilic, 4-hydroxybenzoic, salicyclic, aminosailcylic, embonic, nicotinic, methanesulfonic, ethanesulfonic, hydroxy-ethanesulfonic, ethylenesulfonic, benzenesulfonic, halogenbenzenesulfonic, toluensulfonic, naphthalenesulfonic and sulfanilic acid; methionine, tryptophan, lysine and arginine.

These or other salts, for example, the picrates, can also be used for purification of the bases obtained; the bases are converted into salts, the salts are separated and the bases are liberated from the salts. In view of the close relationship between the free compounds and the compounds in the form of their salt, whenever a compound is referred to in this context, a corresponding salt is also intended, provided such is possible or appropriate under the circumstances.

The new 1,4-dihydropyridine derivatives according to the invention possess valuable pharmacological properties, Because of their influence on the circulatory system, they can be used as antihypertensive agents, as vasodilators and as coronary therapeutic agents and are thus to be regarded as an enrichment of pharmacy.

The synthesis of the compounds according to the invention using dimethylformamide dimethyl acetal and 2-amino-4-(2'-nitorphenyl)-6-methyl-1,4-dihydropyridine-3,5-dicarboxylic acid dimethyl ester can be represented by the following equation:

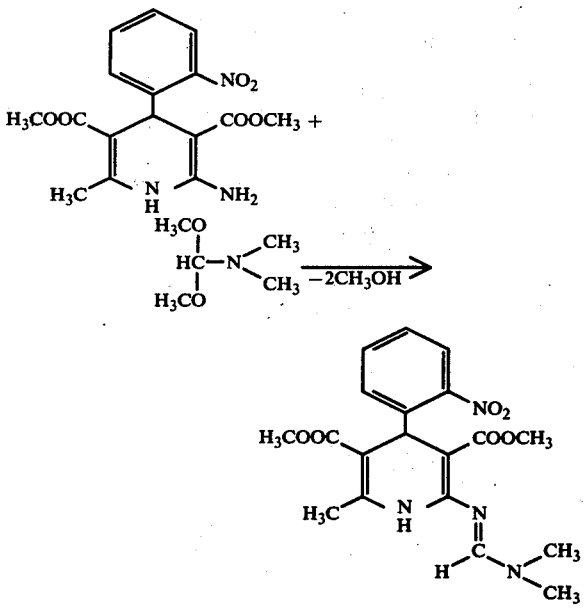

According to the procedure indicated above, a 2-amino-1,4-dihydropyridine of the formula II

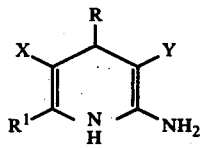

is reacted with an acid amide derivative, in particular with orthocarboxylic acid amide diesters (amide acetals) of the formula IV

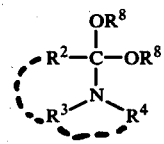

In formula II

R preferably represents a phenyl or naphthyl radical or a thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, quinazolyl or quinoxalyl radical. The heterocyclic radicals mentioned and, in particular, the phenyl radical can carry 1 to 3 identical or different substituents, substituents which may be mentioned being, preferably, phenyl, straight-chain or branched alkyl with 1 to 8, in particular 1 to 4, carbon atoms, alkylene with 3 to 5 carbon atoms, cycloalkyl with 3 to 7 carbon atoms, alkenyl or alkinyl with 2 to 6 carbon atoms, in particular 2 to 3 carbon atoms, alkoxy with preferably 1 to 4, in particular 1 to 2, carbon atoms, dioxyalkylene with 1 to 2 carbon atoms, alkenoxy and alkinoxy with 2 to 6, in particular 3 to 5, carbon atoms, halogen, such as fluorine, chlorine, bromine or iodine, especially fluorine, chlorine or bromine, trifluoromethyl, trifluoromethoxy, nitro, cyano, azido, dialkylamino with preferably 1 to 4, in particular 1 to 2, carbon atoms per alkyl group, carbalkoxy with preferably 2 to 4, in particular 2 or 3, carbon atoms or $SO_m$-alkyl, wherein m denotes a number from 0 to 2 and alkyl preferably contains 1 to 4, in particular 1 or 2, carbon atoms.

Furthermore, in formula II, the radicals X and Y, which can be identical or different, represent the groups —S(O)$_n$—R$^5$ or —CO—R$^6$,
wherein n denotes 0, 1 or 2.

R$^5$ represents a straight-chain, branched or cyclic, saturated or unsaturated aliphatic hydrocarbon radical which is optionally interrupted by 1 to 2 oxygen atoms in the chain or ring or in which a hydrogen atom can be replaced by a phenoxy or phenyl group, which is optionally substituted by halogen, such as fluorine, chlorine or bromine, cyano, dialkylamino with 1 to 2 carbon atoms per alkyl group in each case, alkoxy with 1 to 4 carbon atoms, alkyl with 1 to 4 carbon atoms, trifluoromethyl or nitro, or by an α-, β- or γ-pyridyl group or by an amino group, this amino group carrying two identical or different substituents from the group alkyl with up to 4 carbon atoms, alkoxyalkyl with up to 4 carbon atoms phenyl and aralkyl, in particular benzyl, and these substituents optionally forming, with the nitrogen atom, a 5- to 7-membered ring which can contain an oxygen or sulphur atom as a further heteroatom, or represents an aryl radical, in particular a phenyl radical, which can optionally carry 1 to 3 identical or different substituents, substituents which may be mentioned being straight-chain or branched alkyl with 1 to 4 carbon atoms, alkoxy with 1 to 2 carbon atoms, halogen, such as fluorine, chlorine or bromine, cyano, trifluoromethyl, trifluoromethoxy, dialkylamino with 1 to 2 carbon atoms per alkyl group in each case or nitro, and R$^6$ represents a straight-chain or branched alkyl radical with 1 to 4 carbon atoms, a phenyl radical, a benzyl radical or a dialkylamino group with up to 4 carbon atoms per alkyl group, the alkyl groups optionally forming, with the nitrogen atom, a 5- to 7-membered ring which can contain an oxygen or sulphur atom as a further hetero-atom, or represents the group OR$_7$,
in which R$^7$ represents a straight-chain, branched or cyclic, saturated or unsaturated hydrocarbon radical with up to 8 carbon atoms which is optionally interrupted by 1 or 2 oxygen atoms in the chain or ring or in which a hydrogen atom can be replaced by a phenoxy or phenyl group which is optionally substituted by halogen, such as fluorine, chlorine or bromine, cyano, dialkylamino with 1 to 2 carbon atoms per alkyl group in each case, alkoxy with 1 to 4 carbon atoms, alkyl with 1 to 4 carbon atoms, trifluoromethyl or nitro, or by an α-, β- or γ-pyridyl group or by an amino group, this amino group carrying two identical or different substituents from the group alkyl with up to 4 carbon atoms, alkoxyalkyl with up to 4 carbon atoms, phenyl and aralkyl, in particular benzyl, and these substituents optionally forming, with the nitrogen atom, a 5 to 7-membered ring which can contain an oxygen or sulphur atom as a further heteroatom.

Furthermore, in formula II,

R$^1$ represents hydrogen, a straight-chain or branched alkyl radical with 1 to 4 carbon atoms, a phenyl radical or a benzyl radical.

The 2-amino-1,4-dihydropyridines of the formula II used as starting materials have already been described in most cases or can be prepared according to known methods by reacting ylidene-carbonyl compounds of the formula VII with enediamino compounds of the formula VIII

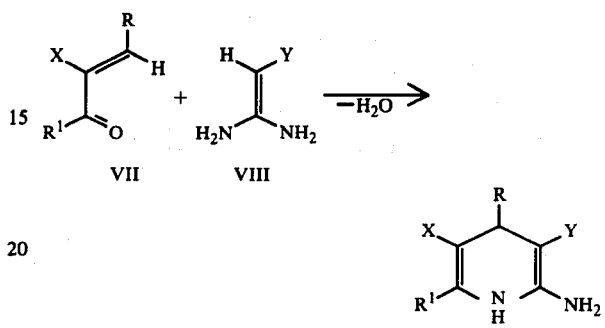

(compare H. Meyer, F. Bossert, W. Vater and K. Stoepel, German Offenlegungsschrift (German Published Specification) No. 2,210,674, publication date: 13.9.1973).

Examples which may be mentioned are: 2-amino-4-(3'-nitrophenyl)-6-methyl-1,4-dihydropyridine-3,5-dicarboxylic acid dimethyl ester, 2-amino-4-(2'-nitrophenyl)-6-methyl-1,4-dihydropyridine-3,5-dicarboxylic acid di-n-butyl ester, 2-amino-4-(2'-trifluoromethylphenyl)-6-methyl-1,4-dihydropyridine-3,5-dicarboxylic acid diisopropyl ester, 2-amino-4-(2'-cyanophenyl)-6-methyl-1,4-dihydropyridine-3,5-dicarboxylic acid diisobutyl ester, 2-amino-4-(3'-nitrophenyl)-6-methyl-1,4-dihydropyridine-3,5-dicarboxylic acid di-β-methoxyethyl ester, 2-amino-3-ethoxycarbonyl-4-(2'-methoxyphenyl)-6-methyl-1,4-dihydro-pyridine-5-carboxylic acid methyl ester, 2-amino-3-ethoxy-carbonyl-4-(2'-chlorophenyl)-6-methyl-1,4-dihydropyridine-5-carboxylic acid isopropyl ester, 2-amino-3-ethoxycarbonyl-4-(3'-cyanophenyl)-6-methyl-1,4-dihydropyridine-5-carboxylic acid isobutyl ester, 2-amino-3-ethoxycarbonyl-4-(4'-dimethylamino-phenyl)-6-methyl-1,4-dihydropyridine-5-carboxylic acid cyclopentyl ester, 2-amino-3-methoxycarbonyl-4-(3'-methylsulphonylphenyl)-6-methyl-1,4-dihydropyridine-5-carboxylic acid benzyl ester, 2-amino-3-methoxycarbonyl-4-(2'-proparfyloxyphenyl)-6-methyl-1,4-dihydropyridine-5-carboxylic acid β-phenoxyethyl ester, 2-amino-3-methoxycarbonyl-4-(2'-nitrophenyl)-6-methyl-1,4-dihydropyridine-5-carboxylic acid pyridyl-3-methyl ester, 2-amino-3-methoxycarbonyl-4-(2'-cyanophenyl)-6-methyl-1,4-dihydropyridine-5carboxylic acid β-dimethylaminoethyl ester, 2-amino-3-methoxycarbonyl-4-(3'-nitrophenyl)-6-methyl-1,4-dihydropyridine-5-carboxylic acid β-N-benzyl-N-methylamino-ethyl ester, 2-amino-3-methoxycarbonyl-4-(pyridyl-3)6 methyl 1,4-dihydropyridine-5-carboxylic acid ethyl ester, 2-amino-3-methoxycarbonyl-4-(pyridyl-2)-6-methyl-1,4-dihydropyridine-5-carboxylic acid isopropyl ester, 2-amino-3-methoxycarbonyl-4-(quinolinyl-4)-6-methyl-1,4-dihydropyridine-5-carboxylic acid β-methoxyethyl ester, 2-amino-3-methoxycarbonyl-4-(thienyl-2-) 6-methyl-1,4-dihydropyridine-5-carboxylic acid cyclopentyl ester, 2-amino-3-methoxycarbonyl-4-(furyl-2)-6-methyl- 1,4-dihydropyridine-5-carboxylic acid n-butyl ester, 2-amino-3-phenylsulphonyl-4-(2'-nitrophenyl)-6-methyl-1,4-dihydro-pyridine-5-carboxylic acid methyl ester and 2-amino-4-(3'-nitrophenyl)-5-methylsulphonyl-6-methyl-1,4-dihydropyridine-3-carboxylic acid methyl ester.

In the formula IV, $R^8$ preferably represents a lower alkyl radical with 1 to 4, in particular 1 to 2, carbon atoms, $R^2$ preferably represents hydrogen or a straight-chain or branched alkyl radical with up to 8 carbon atoms, in particular with up to 4 carbon atoms, it being possible for the alkyl radical optionally to form, together with the structural fragment —C—N—$R^3$—, a five-membered to seven-membered heterocyclic ring in the manner indicated, and the radicals $R^3$ and $R^4$, which can be identical or different, represent a straight-chain or branched alkyl radical with up to 8 carbon atoms, in particular with up to 4 carbon atoms, an alkoxyalkyl radical with up to 6 carbon atoms, in particular with up to 4 carbon atoms, or an aralkyl adical, in particular a benzyl radical, it being possible for the alkyl groups to form, with the nitrogen atom, a =- to 7-membered ring which can optionally contain an oxygen or sulphur atom as a further hetero-atom.

The amide acetals of the formula IV used as starting materials are already known from the literature or can be prepared by methods known from the literature (compare, for example, H. Meerwein, W. Florian, N. Schön and G. Stopp, Liebigs Ann. Chem. 641, 1 et seq. (1961)).

Examples which may be mentioned are: dimethylformamide dimethyl acetal, dimethylformamide diethyl acetal, dimethylformamide di-n-butyl acetal, dimethylformamide di-β-methoxy-ethyl acetal, piperidinodiethoxymethane, morpholinodiethoxymethane, dimethylacetamide diethyl acetal, butyric acid dimethylamide diethyl acetal, isobutyric acid dimethylamide diethyl acetal, N-methyl-pyrrolidone-2 diethyl acetal, N-methyl-piperidinone-2-diethyl acetal and N-methyl-ε-caprolactam diethyl acetal.

The reaction can be carried out both with and without diluents. Diluents which can be used are all the inert organic solvents. These include, preferably, hydrocarbons, such as benzine, benzene or toluene, chlorinated hydrocarbons, such as methylene chloride, chloroform, chloroform, carbon tetrachloride or chlorobenzene, alcohols, such as methanol, ethanol or butanol, ethers, such as diethyl ether, dioxane, tetrahydrofurane, glycol monomethyl ether or glycol dimethyl ether, and furthermore dimethylformamide, dimethylsulphoxide, acetonitrile, pyridine and hexamethylphosphoric acid triamide.

The reactin temperatures can be varied within a fairly wide range. In general, the reaction mixture is heated to temperatures between 50° and 150° C.

The reaction can be carried out under normal pressure, but also under elevated pressure. In general, it is carried out under normal pressure.

In carrying out the process according to the invention, one mole of the 2-amino-1,4-dihydropyridine of the formula II is reacted with 1 to 2 mols of the amide acetal of the formula IV. The reaction products, which in most cases are obtained in crystalline form, are suspended in a little ether, filtered off and, for purification, recrystallised from a suitable solvent.

The above preparation process is only given for illustration and the preparation of the compounds of the formula I is not limited to ths process but any modification of this process can be used, in the same manner, for the preparation of the compounds according to the invention.

The compounds according to the invention can exist in stereoisomeric forms which either behave as mirror images of one another (enantiomers) or do not behave as mirror images of one another (diastereomers). The present invention relates to both the antipodes and the racemic forms as well as the diastereomer mixtures. They can be separated into the stereoisomerically uniform constituents in a known manner (compare, for example, E.L. Eliel, Stereochemistry of Carbon Compounds, McGraw Hill, 1962).

In addition to the preparation examples given below, the following active compounds according to the invention may be mentioned: 2-(dimethylaminomethyleneamino)-4-(2'-nitrophenyl)-6-methyl-1,4-dihydropyridine-3,5-dicarboxyic acid dimethyl ester, 2-(dimethylaminomethyleneamino)-4-(2'-trifluoromethylphenyl)-6-methyl-1,4-dihydropyridine-3,5-dicarboxylic acid diethyl ester, 2-(dimethylaminomethyleneamino)-3-methoxycarbonyl-4-(3'-nitrophenyl)-6-methyl-1,4-dihydroyridine-5-carboxylic acid ethyl ester, 2-(dimethylaminomethyleneamino)-3-methoxycarbonyl-4-(3'-nitrophenyl)-6-methyl-1,4-dihydropyridine-5-carboxyic acid isopropyl ester, 2-(dimethylaminomethyleneamino)-3-methoxycarbonyl-4-(2'-trifluoromethylphenyl)-6-methyl-1,4-dihydropyridine-5-carboxylic acid cyclopentyl ester, 2-(dimethylaminomethyleneamino)-3-methoxycarbonyl-4-(3'-nitrophenyl)-6-methyl-1,4-dihydro-pyridine-5-carboxylic acid β-methoxyethyl ester, 2-(dimethyl-aminomethyleneamino)-3-methoxycarbonyl-4-(3'-methylsulphonyl-phenyl)-6-methyl-1,4-dihydropyridine-5-carboxylic acid β-phenoxyethyl ester, 2-(dimethylaminomethyleneamino)-3-methoxy-carbonyl-4-(2'-cyanophenyl)-6-methyl-1,4-dihydropyridine-5-carboxylic acid (β-(pyridyl-2)-ethyl ester, 2-(dimethylaminomethyleneamino)-3-methoxycarbonyl-4-(2'-methylphenyl)-6-methyl-1,4-dihydropyridine-5-carboxylic acid benzyl ester, 2-(dmethyl-aminomethyleneamino)-3-methoxycarbonyl-4-(2'-nitrophenyl)-6-ethyl-1,4-dihydropyridine-5-carboxylic acid (4-trifluoro-methylbenzyl) ester, 2-(dimethylaminomethyleneamino)-3-methoxy-carbonyl-4-(3'-nitrophenyl)-6-methyl-1,4-dihydropyridine-5-carboxyic acid β-dimethylamino-ethyl ester, 2-(dimethylaminomethyleneamino)-3-methoxycarbonyl-4-(3'-nitrophenyl)-6-methyl-1,4-dihydropyridine-5-caboxylic acid β-N-benzyl-N-mthylamino-ethyl ester, 2-(di-n-butylaminomethyleneamino)-3-methoxycarbonyl-4-(2'-nitrophenyl)-6-methyl-1,4-dihydropyridine-5-carboxylic acid methyl ester, 2-(di-n-butylaminomethyleneamino)-3-methoxycarbonyl-4-(3'-nitrophenyl)-6-methyl-1,4-dihydropyridine-5-carboxylic acid isopropyl ester, 2-(di-n-butylaminomethyleneamino)-3-ethoxycarbonyl-4-(3'-nitrophenyl)-6-methyl-1,4-dihydropyridine-5-carboxylic acid methyl ester, 2-(di-n-butylaminomethyleneamino)-3-ethoxycarbonyl-4-(3'-nitrophenyl)-6-methyl-1,4-dihyropyridine-5-carboxylic acid β-methoxyethyl ester and 2-(di-n-butylaminomethyleneamino)-3-isopropoxycarbonyl-4-(3'-nitrophenyl)-6-methyl-1,4-dihydro-pyridine-5-carboxylic acid methyl ester.

Aminoalkylideneamino-1,4-dihydropyridines of the formula I in which

R represents a phenyl radical which is optionally substituted by nitro, cyano, halogen, especially chlorine, trifluoromethyl, methyl or methoxy or represents a pyridyl or naphthyl radical and X and Y are identical or different and represent the groups $-SO_2-R^5$ or $-CO-R^6$,
wherein $R^5$ represents alkyl with 1 to 4 carbon atoms or phenyl and $R^6$ represents a straight-chain, branched or cyclic alkoxy radical with 1 to 6 carbon atoms which is optionally interrupted in the alkylene chain by a further oxygen atom or represents an alkoxy radical with 2 or 3 carbon atoms which is substituted by dimethylamino or a N-benzyl-N-methylamino group and $R^1$ represents methyl or ethyl, $R^2$ represent hydrogen or alkyl with 1 to 4 carbon atoms and $R^3$ and $R^4$ are identical or different and each represent an alkyl radical, an alkoxyalkyl radical or a benzyl radical or $R^3$ either forms, together with $R^4$, a 5- to 7-membered ring or $R^3$ forms, together with $R^2$, a 5- to 7-membered ring, are of particular importance.

The new compounds are substances which can be used as medicaments. They possess a broad and versatile spectrum of pharmacological activity.

In detail, it was possible to demonstrate the following main actions in animal experiments:

(1) On parenteral, oral and perlingual administration the compounds a distinct and long-lasting dilation of the coronary vessels.

This action on the coronary vessels is intensified by a simultaneous nitrite-like effect of relieving the load on the heart.

They influence or modify the heart metabolism in the sense of an energy saving.

(2) The excitability of the stimulus formation and excitation conduction system within the heart is lowered, so that an anti-fibrillation action which can be demonstrated at therapeutic doses results.

(3) The tone of the smooth muscle of the vessels is greatly reduced under the action of the compounds. This vascular-spasmolytic action can take place in the entire vascular system or can manifest itself more or less isolated in circumscribed vascular regions (such as, for example, the central nervous system).

(4) The compounds lower the blood pressure of normotonic and hypertensive animals and can thus be used as antihypertensive agents.

(5) The compounds have a strongly muscular-spasmolytic action which manifest themselves on the smooth muscle of the stomach, the intestinal tract, the urogenital tract and the respiratory system.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile or isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third, or a quarter of a daily dose will depend on whether the medicament is to be administered once or, for example, twice, three times or four times a day respectively.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferbly in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents; and tablets can be scored to provide for fractioned dosages.

The diluents to be used in pharmaceutical compositions adapted to be formed into suppositories can, for example, be the usual water-soluble or water-insoluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are solutions and emulsions can, for example, contain the customary diluents (with, or course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, the solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminum metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention preferably contain about 0.1 to 99.5, more preferably from about 0.5 to 95% of the active ingredient by weight of the total composition.

In addition to a compound of the invention, the pharmaceutical compositions and medicaments according to the invention and can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging, for medical administration and may be, for example, any of the following: tablets, (including lozenges and granulates), pills, dragees, capsules, suppositories and ampoules. Some, such as capsules, include a protective envelope which renders the portions of the medicament physically discrete and coherent.

The preferred daily dose for administration of the medicaments of the invention is 0.05 mg to 1 g of active ingredient.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of), the above-mentioned diseases in human and non-human animals, which comprises administering to the animals a compound of the invention alone or in admixture with a diluent or in the form of a medicament according to the invention.

It is envisaged that these active compounds will be administered perorally, parenterally (for example intramuscularly, intraperitoneally or intravenously), or rectally, preferably orally or parenterally, especially perlingually or intravenously. Preferred pharmaceutical compositions and medicaments are therefore those adapted for oral or parenteral administration.

In general it has proved advantageous, in the case of intravenous administration, to administer amounts of from 0.001 to 5 mg/kg, preferably from 0.05 to 2 mg/kg of body weight daily to achieve effective results, and in the case of oral administration the dosage is from 0.05 to 10 mg/kg, preferably from 0.5 to 5 mg/kg of body weight daily.

Nevertheless it can at times be necessary to deviate from the amounts mentioned and in particular to do so as a function of the body weight of the test animal or of the nature of the administration route, but also because of the type of animal and its individual behaviour towards the medicament or the nature of its formulation and the time or interval at which it is administered. Thus it may be sufficient, in some cases, to manage with less than the abovementioned minimum amount whilst in other cases the upper limit mentioned must be exceeded. Where larger amounts are administered it can be advisable to divide these into several individual doses over the course of the day. The same dosage range is envisaged for administration in human medicine. Here, again, the general sense of the above comments applies.

Preparation Examples

EXAMPLE 1

2-(Dimethylaminomethyleneamino)-4-phenyl-6-methyl-1,4-dihydropyridine-3,5-dicarboxylic acid diethyl ester

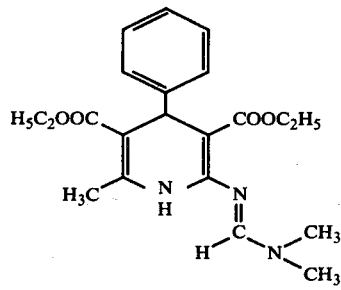

15 g (45 mmols) of 2-amino-4-phenyl-6-methyl-1,4-dihydropyridine-3,5-dicarboxylic acid diethyl ester were warmed to 100° C. together with 10 g (84 mmols) of dimethylformamide dimethyl acetal and the mixture was stirred for about 60 minutes at this temperature. The reaction mass solidified whilst cooling and was suspended in a little ether, filtered off and recrystallised from ethanol. Melting point: 131° C. Yield: 13.7 g (79%)

EXAMPLE 2

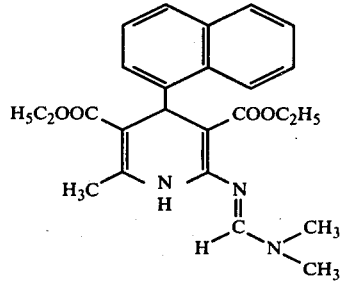

2-(Dimethylaminomethyleneamino)-4-(naphthyl-1)-6-methyl-1,4-dihydropyridine-3,5-dicarboxylic acid diethyl ester of melting point 180° C. (ethanol) was obtained analogously to Example 1 by reacting 45 mmols of 2-amino-4-(naphthyl-1)-6-methyl-1,4-dihydropyridine-3,5-dicarboxylic acid diethyl ester and 84 mmols of dimethylformamide dimethyl acetal. Yield-65% of theory.

EXAMPLE 3

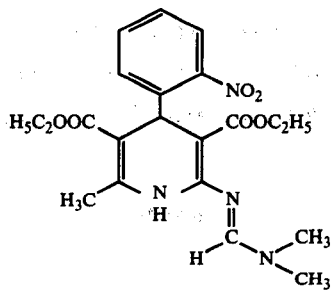

2-(Dimethylaminomethyleneamino)-4-(2'-nitrophenyl)-6-methyl-1,4-dihydropyridine-3,5-dicarboxylic acid diethyl ester of melting point 126° C. (ethanol) was obtained analogously to Example 1 by reacting 45 mmols of 2-amino-4-(2'-nitrophenyl)-6-methyl-1,4-dihydropyridine-3,5-dicarboxylic acid diethyl ester and 84 mmols of dimethylformamide dimethyl acetal. Yield: 70% of theory.

EXAMPLE 4

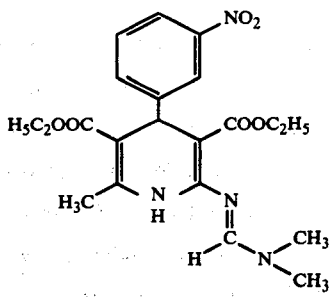

2-(Dimethylaminomethyleneamino)-4-(3'-nitrophenyl)-6-methyl-1,4-dihydropyridine-3,5-dicarboxylic acid diethyl ester of melting point 150° C. (ethanol) was obtained analogously to Example 1 by reacting 45 mmols of 2-amino-4-(3'-nitrophenyl)-6-methyl-1,4-dihydropyridine-3,5-dicarboxylic acid diethyl ester and 84 mmols of dimethylformamide dimethyl acetal. Yield: 73% of theory.

EXAMPLE 5

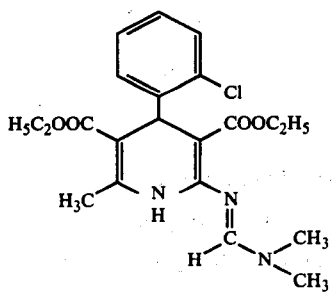

2-(Dimethylaminomethyleneamino)-4-(2'-chlorophenyl)-5-methoxycarbonyl-6-methyl-1,4-dihydropyridine-3-carboxylic acid ethyl ester of melting point 137° (ethanol) was obtained analogously to Example 1 by reacting 45 mmols of 2-amino-4-(2'-chlorophenyl)-5-methoxycarbonyl-6-methyl-1,4-dihydropyridine-3-carboxylic acid ethyl ester and 68 mmols of dimethylformamide diethyl acetal. Yield: 68% of theory.

EXAMPLE 6

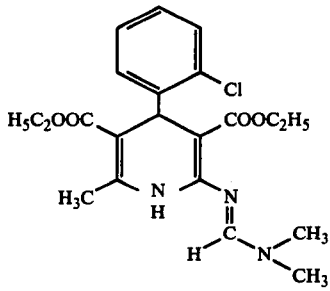

2-(Dimethylaminomethyleneamino)-4-(2'-chlorophenyl)-6-methyl-1,4-dihydropyridine-3,5-dicarboxylic acid diethyl ester of melting point 140° C. (ethanol) was obtained analogously to Example 1 by reacting 45 mmols of 2-amino-4-(2'-chlorophenyl)-6-methyl-1,4-dihydropyridine-3,5-dicarboxylic acid diethyl ester and 68 mmols of dimethylformamide diethyl acetal. Yield: 75% of theory.

EXAMPLE 7

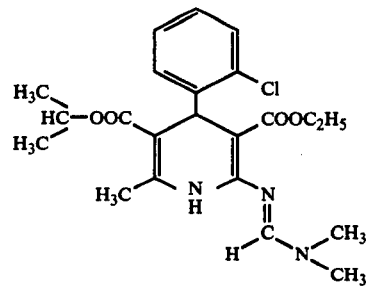

2-(Dimethylaminomethyleneamino)-3-ethoxycarbonyl-4-(2'-chlorophenyl)-6-methyl-1,4-dihydropyridine-5-carboxylic acid isopropyl ester of melting point 138° C. (ethanol) was obtained analogously to Example 1 by reacting 45 mmols of 2-amino-3-ethoxycarbonyl-4-(2'-chlorophenyl)-6-methyl-1,4-dihydropyridine-5-carboxylic acid isopropyl ester and 68 mmols of dimethylformamide diethyl acetal. Yield: 66% of theory.

EXAMPLE 8

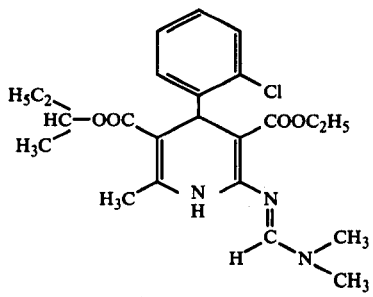

2-(Dimethylaminomethyleneamino)-3-ethoxycarboxyl-4-(2'-chlorophenyl)-6-methyl-1,4-dihydropyridine-5-carboxylic acid sec.-butyl ester of melting point 128° C. (ethanol) was obtained analogously to Example 1 by reacting 45 mmols of 2-amino-3-ethoxycarbonyl-4-(2'-chlorophenyl)-6-methyl-1,4-dihydropyridine-5-carboxylic acid sec.-butyl ester and 68 mmols of dimethylformamide diethyl acetal. Yield 65% of theory

EXAMPLE 9

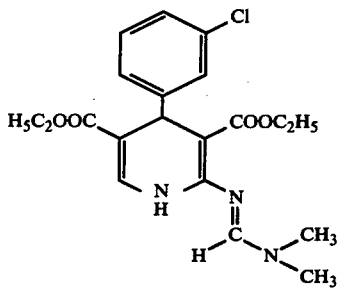

2-(Dimethylaminomethyleneamino)-4-(3'-chlorophenyl)-6-methyl-1,4-dihydropyridine-3,5-dicarboxylic acid diethyl ester of melting point 150° C. (ethanol) was obtained analogously to Example 1 by reacting 45 mmols of 2-amino-4-(3'-chlorophenyl)-6-methyl-1,4-dihydropyridine-3,5-dicarboxylic acid diethyl ester and 68 mmols of dimethylformamide diethyl acetal. Yield: 76% of theory.

EXAMPLE 10

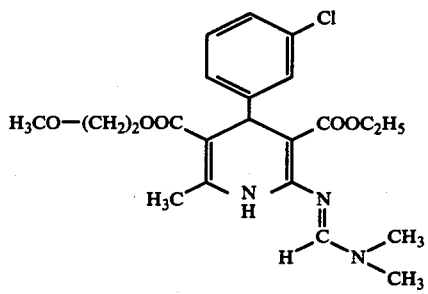

2-(Dimethylaminoethyleneamino)-3-ethoxycarbonyl-4-(3'-chlorophenyl)-6-methyl-1,4-dihydropyridine-5-carboxylic acid β-methoxyethyl ester of melting point 120° C. (ethanol) was obtained analogously to Example 1 by reacting 45 mmols of 2-amino-3-ethoxycarbonyl-4-(3'-chlorophenyl)-6-methyl-1,4-dihydropyridine-5-carboxylic acid β-methoxyethyl ester and 68 mmols of dimethylformamide diethyl acetal. Yield: 65% of theory.

EXAMPLE 11

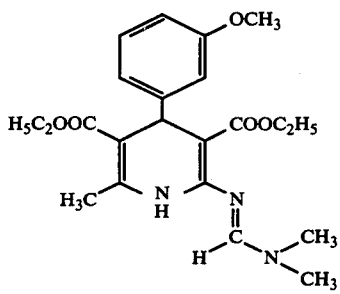

2-(Dimethylaminomethyleneamino)-4-(3'-methoxyphenyl)-6-methyl-1,4-dihydropyridine-3,5-dicarboxylic acid diethyl ester of melting point 136° C. (ethanol) was obtained analogously to Example 1 by reacting 45 mmols of 2-amino-4-(3'-methoxy-phenyl)-6-methyl-1,4-dihydropyridine-3,5-dicarboxylic acid diethyl ester and 68 mmols of dimethylformamide diethyl acetal. Yield: 70% of theory.

EXAMPLE 12

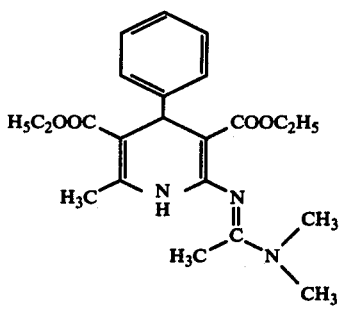

2-(Dimethylamino-ethylideneamino)-4-phenyl-6-methyl-1,4-dihydropyridine-3,5-dicarboxylic acid diethyl ester of melting point 126° C. (ethanol was obtained analogously to Example 1 by reacting 45 mmols of 2-amino-4-phenyl-6-methyl-1,4-dihydropyridine-3,5-dicarboxylic acid diethyl ester and 68 mmols of dimethylacetamide diethyl acetal. Yield: 56% of theory.

EXAMPLE 13

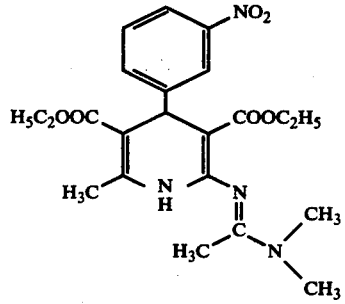

2-(Dimethylamino-ethylideneamino)-4-(3'-nitrophenyl)-6-methyl-1,4-dihydropyridine-3,5-dicarboxylic acid diethyl ester of melting point 172° C. (ethanol) was obtained analogously to Example 1 by reacting 45 mmols of 2-amino-4-(3'-nitrophenyl)-6-methyl-1,4-dihydropyridine-3,5-dicaroxylic acid diethyl ester and 68 mmols of dimethylacetamide diethyl acetal.
Yield: 52% of theory.

EXAMPLE 14

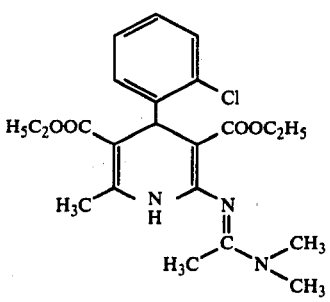

2-(1-Dimethylamino-ethylidenamino)-4-(2'-chlorophenyl)-6-methyl-1,4-dihydropyridine-3,5-dicarboxylic acid diethyl ester of melting point 181° C. (ethanol) was obtained analogously to Example 1 by reacting 45 mmols of 2-amino-4-(2'-chlorophenyl)-6-methyl-1,4-dihydropyridine-3,5-dicarboxylic acid diethyl ester and 68 mmols of dimethylacetamide diethyl acetal.
Yield: 62% of theory.

EXAMPLE 15

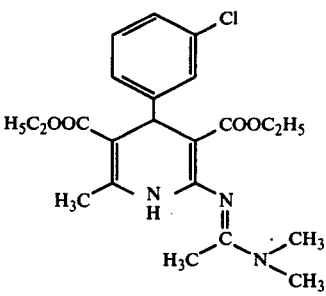

2-(1-Dimethylamino-ethylideneamino)-4-83'-chlorophenyl)-6-methyl-1,4-dihydropyridine-3,5-dicarboxylic acid diethyl ester of melting point 160° C (ethanol) was obtained analogously to Example 1 by reacting 45 mmols of 2-amino-4-(3'-chlorophenyl)-6-methyl-1,4-dihydropyridine-3,5-dicarboxylic acid diethyl ester and 68 mmols of dimethylacetamide diethyl acetal.
Yield: 60% of theory.

EXAMPLE 16

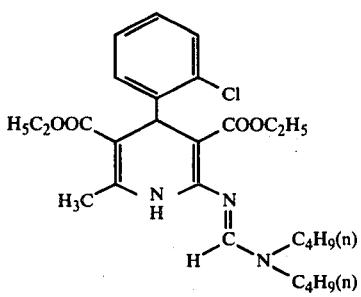

2-(Di-n-butylamino-methyleneamino)-4-(2'-chlorophenyl)-6-methyl-1,4-dihydropyridine-3,5-dicarboxylic acid diethyl ester of melting point 126° C. (ethanol) was obtained analogously to Example 1 by reacting 50 mmols of 2-amino-4-(2'-chloro-phenyl)-6-methyl-1,4-dihydropyridine-3,5-dicarboxylic acid diethyl ester and 87 mmols of di-n-butyl-formamide diethyl acetal.
Yield: 60% of theory.

EXAMPLE 17

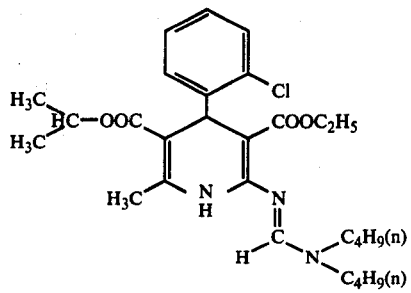

2-(Di-n-butylamino-methyleneamino-3-ethoxycarbonyl-4-(2'chlorophenyl)-6-methyl-1,4-dihydropyridine-5-carboxylic acid isopropyl ester of melting point 126° C. (ethanol) was obtained analogously to Example 1 by reacting 48 mmols of 2-amino-3-ethoxycarbonyl-4-(2'-chlorophenyl)-6-methyl-1,4-dihydropyridine-5-carboxylic acid isopropyl ester and 90 mmols of di-n-butyl-formamide diethyl acetal.
Yield: 56% of theory.

EXAMPLE 18

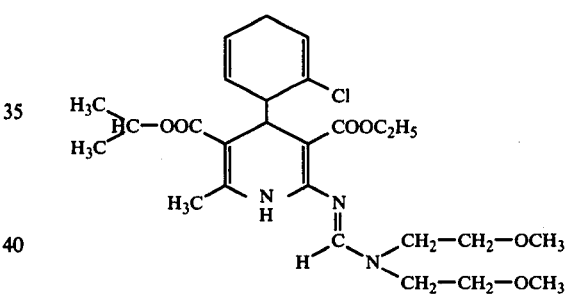

2-(Di-β-methoxyethylamino-methyleneamino)-3-ethoxy-carbonyl-4-(2'-chlorophenyl)-6-methyl-1,4-dihydropyridine-5-carboxylic acid isopropyl ester of melting point 92° C. (ethanol/ether) was obtained analogously to Example 1 by reacting 30 mmols of 2-amino-3-ethoxycarbonyl-4-(2'-chlorophenyl)-6-methyl-1,4-dihydropyridine-5-carboxylic acid isopropyl ester and 50 mmols of di-β-methoxyethyl-formamide diethyl acetal.
Yield: 70% of theory.

EXAMPLE 19

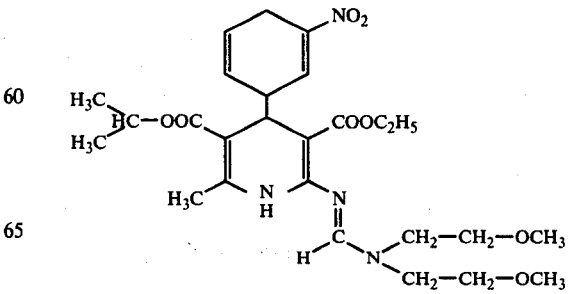

2-(Di-β-methoxyethylamino-methyleneamino)-3-ethoxy-carbonyl-4-(3'-nitrophenyl)-6-methyl-1,4-dihydropyridine-5-carboxylic acid isopropyl ester of melting point 119° C. (ethanol) was obtained analogously to Example 1 by reacting 30 mmols of 2-amino-3-ethoxycarbonyl-4-(3'-nitrophenyl)-6-methyl-1,4-dihydropyridine-5-carboxylic acid isopropyl ester and 50 mmols of di-β-methoxyethyl-formamide diethyl acetal.

Yield: 72% of theory.

EXAMPLE 20

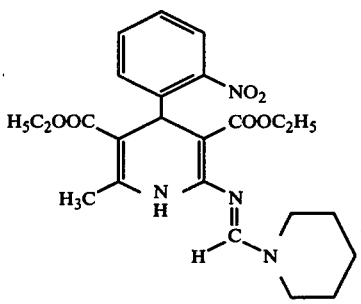

2-(Piperidinomethyleneamino)-4-(2'-nitrophenyl)-6-methyl-1,4-dihydropyridine-3,5-dicarboxylic acid diethyl ester of melting pont 142° C. (ethanol) was obtained analogously to Example 1 by reacting 50 mmols of 2-amino-4(2'-nitrophenyl)-6-methyl-1,4-dihydropyridine-3,5-dicarboxylic acid diethyl ester and 100 mmols of formic acid piperidide diethyl acetal.

Yield: 70% of theory.

EXAMPLE 21

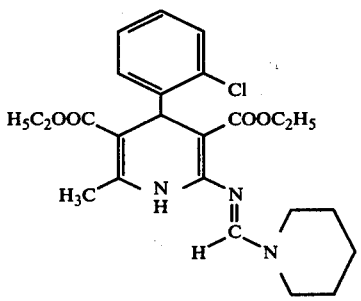

2-(Piperidinomethyleneamino)-4-(2'-chlorophenyl)-6-methyl-1,4-dihydropyridine-3,5-dicarboxylic acid diethyl ester of melting point 145° C. (ethanol) was obtained anaglously to Example 1 by reacting 50 mmols of 2-amino-4-(2'-chlorophenyl)-6-methyl-1,4-dihydropyridine-3,5-dicarboxylic acid diethyl ester and 80 mmols of formic acid piperidide diethyl acetal.

Yield: 63% of theory.

EXAMPLE 22

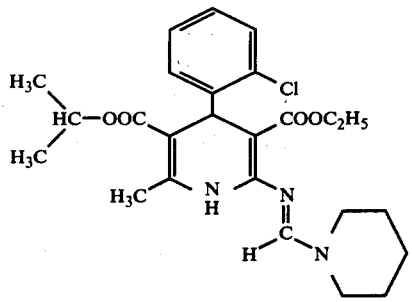

2-(Piperidinomethyleanamino)-3-ethoxycarbonyl-4-(2'-chlorophenyl)-6-methyl-1,4-dihydropyridine-5-carboxylic acid isopropyl ester of melting point 163° C. (ethanol) was obtained analogously to Example 1 by reacting 48 mmols of 2-amino-3-ethoxycarbonyl-4-(2'-chlorophenyl)-6-methyl-1, 4-dihydropyridine-5-carboxylic acid isopropyl ester and 80 mmols of formic acid piperidide diethyl acetal.

Yield: 59% of theory.

EXAMPLE 23

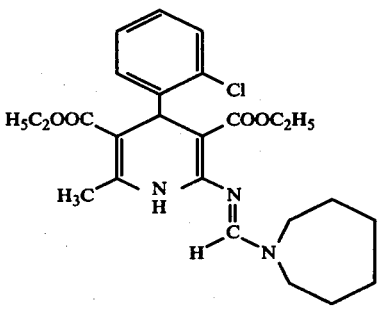

2-(Hexahydroazepino-methyleneamino)-4-(2'-chlorophenyl)-6-methyl-1,4-dihydropyridine-3,5-dicarboxylic acid diethyl ester of melting point 160° C. (ethanol) was obtained analogously to Example 1 by reacting 50 mmols of 2-amino-4-(2'-chlorophenyl)-6-methyl-1,4-dihydropyridine-3,5-dicarboxylic acid diethyl ester and 75 mmols of diethoxyhexahydroazepinomethane.

Yield: 65% of theory.

EXAMPLE 24

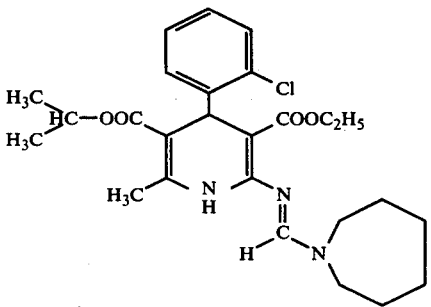

2-(Hexahydroazepinomethyleneamino)-3-ethoxycarbonyl-4-(2'-chlorophenyl)-6-methyl-1,4-dihydropyridine-5-carboxylic acid isopropyl ester of melting point 195° C. (ethanol) was obtained analogously to Example 1 by reacting 50 mmols of 2-amino-3-ethoxycarbonyl-4-(2'-chlorophenyl)-6-methyl-1,4-dihydropyridine-5-carboxylic acid isopropyl ester and 75 mmols of diethoxy-hexahydroazepino-methane.
Yield: 70% of theory.

EXAMPLE 25

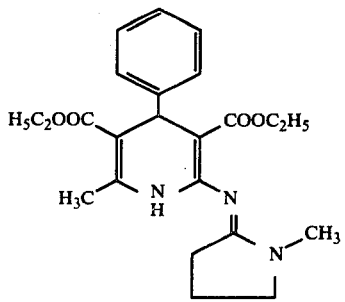

2-(N-Methylpyrrolidinylidene-2-amino)-4-phenyl-6-methyl-1,4-dihydropyridine-3,5-dicarboxylic acid diethyl ester of melting point 133° C. (ethanol) was obtained analogously to Example 1 by reacting 50 mmols of 2-amino-4-phenyl-6-methyl-1,4-dihydropyridine-3,5-dicarboxylic acid diethyl ester and 100 mmols of N-methylpyrrolidone-2diethyl acetal.
Yield: 68% of theory.

EXAMPLE 26

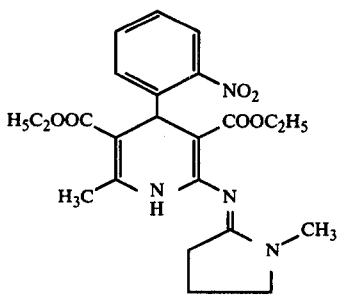

2-(N-Methylpyrrolidinylidene-2-amino)-4-(2'-nitrophenyl)-6-methyl-1,4-dihydropyridine-3,5-dicarboxylic acid diethyl ester of melting point 144° C. (ethanol) was obtained analogously to Example 1 by reacting 38 mmols of 2-amino-4-(2'-nitrophenyl)-6-methyl-1,4-dihydropyridine-3,5-dicarboxylic acid diethyl ester and 100 mmols of N-methylpyrrolidone-2-diethyl acetal.
Yield: 72% of theory.

EXAMPLE 27

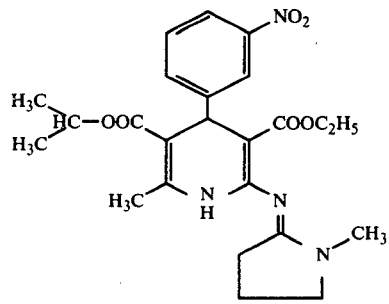

2-(N-Methylpyrrolidinylidene-2-amino)-3-ethoxycarbonyl-4-(3'-nitrophenyl)-6-methyl-1,4-dihydropyridine-5-carboxylic acid isopropyl ester of melting point 135° C. (ethanol) was obtained analogously to Example 1 by reacting 50 mmols of 2-amino-3-ethoxycarbonyl-4-(3'-nitrophenyl)-6-methyl-1,4-dihydro-pyridine-5-carboxylic acid isopropyl ester and 100 mmols of N-methylpyrrolidone-2-acetal.
Yield: 66% of theory.

EXAMPLE 28

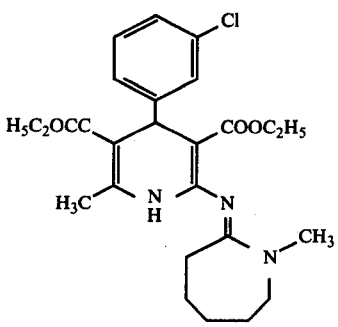

2-(N-Methylhexahydroazepinylidene-2-amino)-4-(3'-chlorophenyl)-6-methyl-1,4-dihydropyridine-3,5-dicarboxylic acid diethyl ester of melting point 104° C. (ethanol) was obtained analogously to Example 1 by reacting 40 mmols of 2-amino-4-(3'-chlorophenyl)-6-methyl-1,4-dihydropyridine-3,5-dicarboxylic acid diethyl ester and 70 mmols of N-methyl-ε-caprolactam diethyl acetal.
Yield 62% of theory.

EXAMPLE 29

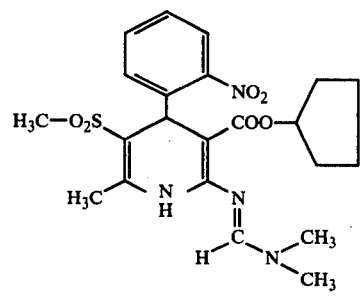

2-(Dimethylaminomethyleneamino)-4-(2'-nitrophenyl)-5-methylsulphonyl-6-methyl-1,4-dihydropyridine-3-carboxylic acid cyclopentyl ester of melting point 175° C. (ethanol) was obtained analogously to Example 1 by reacting 40 mmols of 2-amino-4(2'-nitrophenyl)-5-methylsulphonyl-6-methyl-1,4-dihydropyridine-3-carboxylic acid cyclopentyl ester and 65 mmols of dimethyl-formamide diethyl acetal. Yield: 68% of theory.

EXAMPLE 30

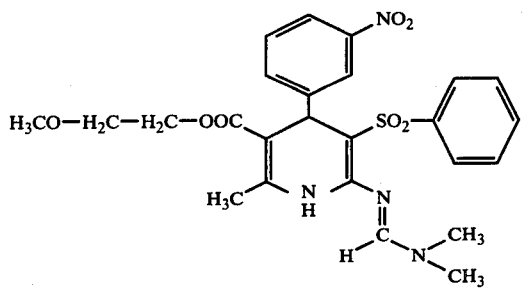

2-(Dimethylaminomethyleneamino)-3-phenylsulphonyl-4-(3'-nitrophenyl)-6-methyl-1,4-dihydropyridine-5-carboxylic acid β-methoxyethyl ester of melting point 226° C. (ethanol) was obtained analogously to Example 1 by reacting 20 mmols of 2-amino-3-phenylsulphonyl-4-(3'-nitrophenyl)-6-methyl-1, 4-di-hydropyridine-5-carboxylic acid β-methoxyethyl ester and 40 mmols of dimethylformamide diethyl acetal. Yield 66% of theory.

What we claim is:

1. An aminoalkylideneamino-1,4-dihydropyridine of the formula I

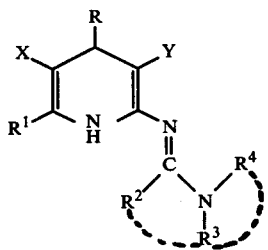

in which

R represents phenyl or naphthyl, which is unsubstituted or substituted by 1 to 3 identical or different substituents selected from phenyl, straight-chain or branched alkyl with 1 to 8 carbon atoms, alkylene with 3 to 5 carbon atoms, cycloalkyl with 3 to 7 carbon atoms, alkenyl or alkinyl with 2 to 6 carbon atoms respectively, alkoxy with 1 to 4 carbon atoms, dioxalkylene with 1 to 2 carbon atoms, alkenoxy and alkinoxy with 2 to 6 carbon atoms respectively, halogen, trifluoromethyl, trifluoromethoxy, nitro, cyano, azido, dialkylamino with 1 to 4 carbon atoms per alkyl group, carbalkoxy with 2 to 4 carbon atoms and $SO_m$-alkyl, (where m denotes 0, 1 or 2 and the alkyl group contains 1 to 4 carbon atoms.

$R^1$ represents hydrogen, a straight-chain or branched alkyl radical with 1 to 4 carbon atoms, a phenyl radical or a benzyl radical, $R^2$ represents hydrogen or a straight-chain or branched alkyl radical with 1 to 8 carbon atoms, or represents a benzyl radical and $R^3$ and $R^4$ are identical or different and each represents a striaght-chain or branched alkyl radical having up to 8 carbon atoms, an alkoxyalkyl radical having up to 6 carbon atoms or a benzyl radical, X and Y are identical or different and each represents the group $—SO(0)_n-R^5$ or $—CO—R^6$, wherein n represents 0, 1 or 2, $R^5$ represents alkyl with 1 to 4 carbon atoms or phenyl and $R^6$ represents a straight-chain, branched or cyclic alkoxy radical with 1 to 6 carbon atoms which is optionally interrupted in the alkylene chain by a further oxygen atom or represents an alkoxy radical with 2 or 3 carbon atoms which is substituted by dimethylamino or an N-benzyl-N-methylamino group.

2. A compound of claim 1 which is 2-(dimethylaminomethyleneamino)-4-(2'-chlorophenyl)-5-methoxycarbonyl-6-methyl-1,4-dihydropyridine-3-carboxylic acid ethyl ester.

3. A pharmaceutical composition for combating circulatory diseases by influencing blood vessels in warm blooded animals comprising as an active ingredient an effect amount of a compound of claim 1, in admixture with pharmaceutically compatible a solid or liquefield gaseous diluent or in admixture with a liquid diluent other than a solvent of a molecular weight less than 200 except in the presence of a surface-active agent.

4. A pharmaceutical composition comprising as an active ingredient an effective amount of a compound of claim 3 in the form of a sterile or isotanic aqueous solution.

5. A composition of claim 3 comprising from 0.5 to 95% by weight of said active ingredient.

6. A composition of claim 4 comprising from 0.5 to 95% by weight of said active ingredient.

7. A pharmaceutical composition in dosage unit form comprising an effective amount of a compound of claim 3 together with an inert pharmaceutical carrier.

8. A pharmaceutical composition of claim 7 in the form of tablets, pills, dragees, capsules, ampoules, or suppositories.

9. A method of combating circuilatory disesases by influencing the blooe vessels in warm blooded animals which comprises administering to said animals an effective amount of a compound of claim 1 either alone or in admixture with a diluent or in the form of a medicament.

10. A method of claim 9 in which the active compound is administered in an amount of from 0.001 to 10 mg per kg body weight per day.

11. A method of claim 9 in which the active compound is administered orally or parenterally.

12. A method of claim 10 in which the active compound is administered orally or parenterally.

* * * * *

UNITED STATES PATENT AND TRADEMARK OFFICE
CERTIFICATE OF CORRECTION

PATENT NO. : 4,146,627

DATED : March 27, 1979

INVENTOR(S) : Wehinger, et al.

It is certified that error appears in the above-identified patent and that said Letters Patent are hereby corrected as shown below:

Column 2, line 18 "represnts" should be --represents--.

Column 3, line 50, "aminosailcylic" should be --aminosalicylic--.

Column 7, line 21, "adical" should be --radical--

Column 7, line 23 " ≋ " should be --5--.

Column 7, line 47, "chloroform" repeated

Column 8, line 19, "dicarboxyic" should be --dicarboxylic--

Column 8, line 27, "carboxyic" should be --carboxylic--

Column 8, line 48, "carboxyic" should be --carboxylic--

Column 8, line 51 "mthyl" should be --methyl--

Column 9, line 32, "produce" omitted after "compounds"

UNITED STATES PATENT AND TRADEMARK OFFICE
CERTIFICATE OF CORRECTION

PATENT NO. : 4,146,627
DATED : March 27, 1979
INVENTOR(S) : Wehinger, et al.

It is certified that error appears in the above-identified patent and that said Letters Patent are hereby corrected as shown below:

Column 15, line 15, H$_3$C omitted at 

Column 15, line 43 "Dimethylaminoethyleneamine" should read -- Dimethylaminomethyleneamino --.

Column 16, line 65, "dicaroxylic" should be --dicarboxylic--

Column 17, line 40, "8" should be --(--.

Column 19, line 34 "pont" should be --point--.

Column 22, line 9, "diethyl" omitted before "acetal".

Column 23, line 49 "dioxalkylene" should be --dioxyalkylene--.
Column 24, line 4, "striaght" should be --straight--.
Column 24, line 47, "blooe" should be --blood--.

Signed and Sealed this

Seventh Day of August 1979

[SEAL]

Attest:

LUTRELLE F. PARKER
Attesting Officer   Acting Commissioner of Patents and Trademarks